(12) United States Patent
Nakatuka et al.

(10) Patent No.: US 6,859,990 B2
(45) Date of Patent: Mar. 1, 2005

(54) CHARACTERISTICS EVALUATION METHOD OF INTERMEDIATE LAYER CIRCUIT

(75) Inventors: Shigenori Nakatuka, Hiroshima (JP); Akira Inoue, Tokyo (JP); Kenichiro Choumei, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 275 days.

(21) Appl. No.: 10/245,675

(22) Filed: Sep. 18, 2002

(65) Prior Publication Data

US 2003/0162310 A1 Aug. 28, 2003

(30) Foreign Application Priority Data

Feb. 26, 2002 (JP) .......................... 2002-049263

(51) Int. Cl.[7] .............................. G10R 3/00; G05F 7/00; H01H 15/00
(52) U.S. Cl. .................. 29/593; 29/592.1; 219/121.69; 219/121.83; 228/103; 228/104; 451/5; 451/41
(58) Field of Search ................................ 29/592.1, 593; 219/121.69, 121.83; 228/103, 104; 451/5, 41

(56) References Cited

U.S. PATENT DOCUMENTS

| 6,441,337 B1 | * | 8/2002 | Isaji et al. | ............. | 219/121.62 |
| 6,720,522 B2 | * | 4/2004 | Ikegami et al. | ........ | 219/121.69 |
| 6,750,422 B2 | * | 6/2004 | Gaku et al. | ............. | 219/121.69 |

FOREIGN PATENT DOCUMENTS

| JP | 5-55724 | 3/1993 | | |
| JP | 06077652 A | * 3/1994 | ............ | H05K/3/46 |
| JP | 6-237122 | 8/1994 | | |
| JP | 11-74416 | 3/1999 | | |

OTHER PUBLICATIONS

"Via hole, bond wire and shorting pin modeling for multi-layered circuits"; Ming–Ju Tsai; Tzyy–Sheng Horng; Alexopoulos, N.G.; Microwave Symposium Digest, IEEE MTT–S International, May 23–27 1994; pp. 1777–1780.*

Inoue, Akira et al., "High–Efficiency 0.1cc Power Amplifier Module for 900 MHz Personal Digital Cellular Telephones", IEICE Transactions on Electronics, vol. E82–C, No. 11, Nov. 1999.

* cited by examiner

Primary Examiner—Paul D Kim
(74) Attorney, Agent, or Firm—Leydig, Voit & Mayer, Ltd.

(57) ABSTRACT

The circuit characteristics of an intermediate layer between an uppermost layer and a lowermost layer of a ceramic multilayer substrate with substrates laminated can be evaluated. A method for evaluating the characteristics of the intermediate layer circuit is provided. The intermediate layer circuit is installed on the intermediate layer of the multilayer substrate and has a wiring and a grounding pad, holding grounding potential, formed in the vicinity of the wiring. The method includes steps of: irradiating a region of the upper layer substrate located above the grounding pad of the intermediate layer with a laser to ablate material to a predetermined thickness; polishing the upper layer substrate ablated to the predetermined thickness with a hard polishing tool to expose the wiring and/or grounding pad; and bringing a probe needle in contact with the exposed wiring and/or grounding pad to evaluate characteristics of the intermediate layer circuit.

6 Claims, 5 Drawing Sheets

CHARACTERISTICS EVALUATION METHOD OF INTERMEDIATE LAYER CIRCUIT

BACKGROUND OF THE INVENTION

1. Field of the Invention

The present invention relates to an evaluation of wiring patterns of multilayer ceramic substrates.

2. Description of Background Art

FIG. 1 is a perspective view showing a configuration of a conventional ceramic multilayer substrate 50. Ceramic multilayer substrate 50 has the third layer 53, the second layer 52, and the first layer 51 laminated successively from the bottom, and lastly cap 55 is attached. The figure shows the configuration of the top layer (first layer) 51 before cap 55 is attached. The first layer 51 includes the top wiring and chip part 54. The same thing can be said of the second layer 52 and the third layer 53.

FIG. 2 is a cross-sectional view of ceramic multilayer substrate 50 cut in the direction perpendicular to each layer. Wiring 64 of the first layer 51 (FIG. 1), wiring 65 of the second layer 52 (FIG. 1), and inner wiring 66 of the third layer 53 (FIG. 1) are circuit wiring of power supply circuit, RF wiring, connection wiring between circuits, etc., respectively. The power supply circuit of the first layer 51 (FIG. 1) is formed using chip parts of resistance R, capacitance C, impedance L, and others. Electrical connections of wiring of each layer are secured by via-holes (for example, via-hole 68).

At the center of ceramic multilayer substrate 50, one or more holes are provided in advance so that semiconductor element 61 may be assembled. More precisely, since the profile of semiconductor element 61, position of via-holes, and other physical conditions differ layer by layer, specified holes must be provided in advance in assembling ceramic multilayer substrate 50. Consequently, before hardening by firing, wiring is put between ceramic materials of, for example, clay, and the holes at the center section and via-holes are formed. Each ceramic layer thus formed is completed by firing. When each ceramic layer is laminated, semiconductor element 61 arranged at the hole is connected to the specified layer (for example, wiring 65 of the second layer 52 (FIG. 1)) by wire 62.

On a surface exposed to the outside of the third layer 53 (FIG. 1), that is, the surface on the side opposite to cap 55, wiring 67 and terminal 69 are mounted. Grounding wiring 67 for multilayer substrate 50 secures grounding. Terminal 69 is, for example, for outputting electric power to secure electrical connections between ceramic multilayer substrate 50 and the outside.

Because in ceramic multilayer substrate 50, wiring is inspected only from wiring 64 on the uppermost layer, the characteristics of intermediate wiring are unable to be directly confirmed and mutual influences between circuits are unable to be evaluated. The reasons are described as follows. Firstly, in ceramic multilayer substrate 50, it is difficult to bore holes to the intermediate layer hardened after firing and process holes without cutting wiring on intermediate layers. Secondly, because if wiring is inspected from wiring 64 on the uppermost layer where a probe needle is brought in contact with the wiring, measurement errors increase and the S parameter is unable to be measured, evaluation cannot be made unless bonding is made on the special-purpose substrate in the module condition. Furthermore, from wiring 64 on the uppermost layer, only direct current characteristics can be evaluated.

SUMMARY OF THE INVENTION

It is an object of the present invention to directly evaluate circuit characteristics of intermediate layers of a ceramic multilayer substrate.

The method according to the present invention can be used for evaluate characteristics of an intermediate layer circuit located between an uppermost layer and a lowermost layer of a multilayer substrate with multiple substrates laminated. The intermediate layer circuit includes a wiring and a grounding pad, having grounding potential, formed in the vicinity of the wiring. The method includes: irradiating a region of an upper layer substrate located above the grounding pad of the intermediate layer with laser to scrape to a predetermined thickness; polishing the upper layer substrate scraped to the predetermined thickness with a hard polishing tool to expose at least one of the wiring and the grounding pad; and bringing a probe needle in contact with the at least one of the exposed wiring and the exposed grounding pad to evaluate characteristics of the intermediate layer circuit.

According to the present invention, because the top substrate is scraped using laser and hard polishing tool to bore holes to the intermediate layer, it is possible to expose wiring, pads, etc. on the intermediate layer without damaging them. Furthermore, because it is possible to bring a probe needle for evaluation directly in contact with wiring, etc. of the exposed intermediate layer through the hole, circuit characteristics can be evaluated reliably and easily.

On the top substrate, the predetermined circuit may be provided on the upper layer substrate, and the predetermined circuit may be arranged with care to avoid a region of the upper layer substrate located above the grounding pad of the intermediate layer. That is, to the region of the top layer substrate to which laser is applied, no circuit is arranged. Therefore, holes can be bored to the intermediate layer without damaging circuit elements of the top layer circuit.

After exposing the wiring and the grounding pad by the exposing step, the method may further include a step of electrically connecting the exposed wiring and the exposed grounding pad using a circuit element. The wiring may include two wiring elements isolated from each other, which are exposed by the exposing step. The method may further includes a step of electrically connecting the exposed two wiring elements using a circuit element. By electrically connecting the exposed wiring and grounding pad or exposed two wiring elements using circuit elements, it is possible to form, for example, a new circuit with the intermediate circuit adjusted.

The laser may be excimer laser. Therefore, it is possible to eliminate detrimental effects of heat on intermediate layer substrates and top layer substrate, and to achieve subtle processing.

The polishing tool may be a diamond bar. Therefore, it is possible to reliably polish ceramic substrates.

BRIEF DESCRIPTION OF THE DRAWINGS

This and other objects and features of the present invention will become clear from the subsequent description of a preferred embodiment thereof made with reference to the accompanying drawings, in which like parts are designated by like reference numerals and in which.

DETAILED DESCRIPTION OF THE PREFERRED EMBODIMENTS

Figure 3:
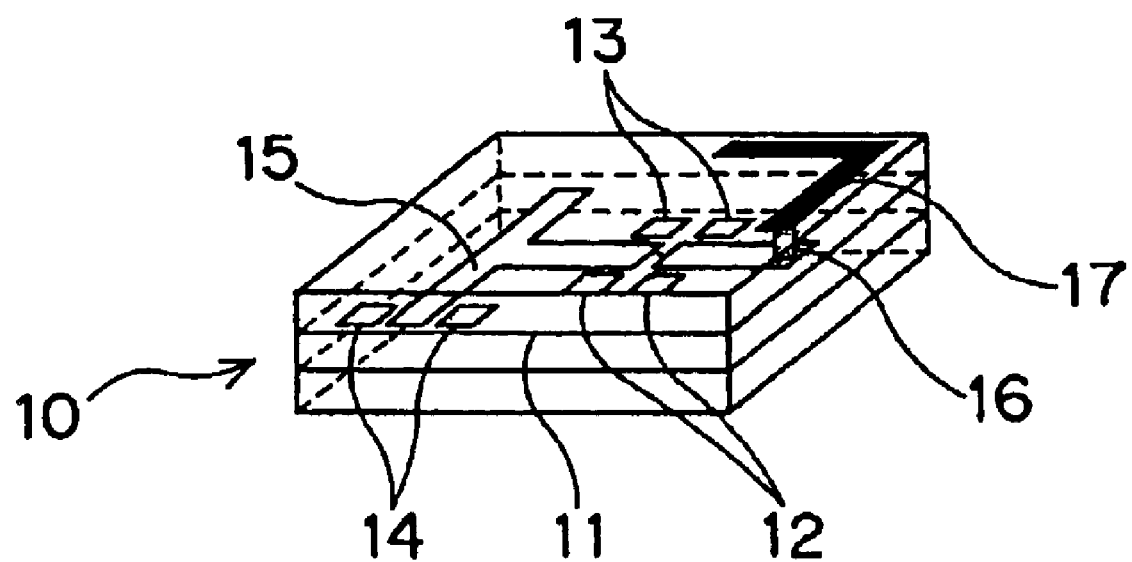
FIG. 3 is a perspective view of ceramic multilayer substrate according to the present invention.

Referring now to the drawings attached, the preferred embodiments of the present invention will be described. FIG. 3 is a perspective view showing the configuration of ceramic multilayer substrate 10 according to the present invention. Ceramic multilayer substrate 10 achieves the specified functions, for example, functions as a power module for controlling the electric power supplied to the outside, in accordance with motions of semiconductor elements (not illustrated) mounted inside.

Ceramic multilayer substrate 50 illustrated includes three layer. To the uppermost layer of the figure, grounding metal wiring 17 which grounds ceramic multilayer substrate 10 is installed. To the uppermost layer, wiring, terminal, element, etc. other than grounding metal wiring 17 can be provided, and to the lowermost layer, required wiring, terminal, element, etc. can be mounted, but nothing particular is specified in the figure.

Figure 4:
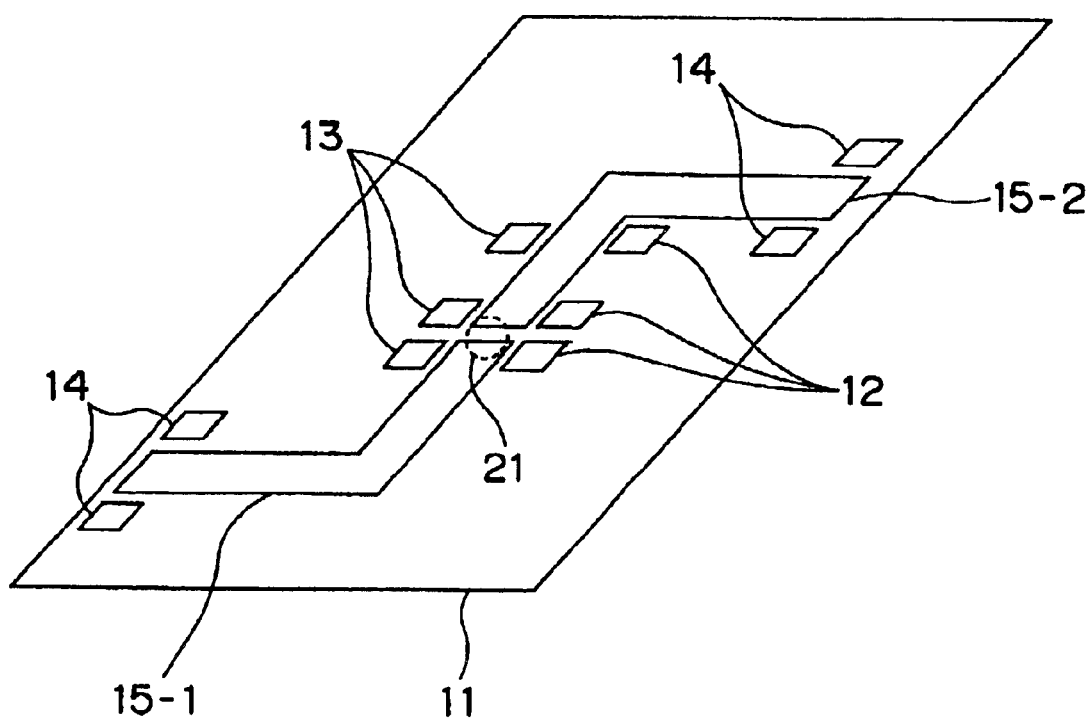
FIG. 4 is a perspective view of a specific configuration of the intermediate layer.

To intermediate layer 11 located between the uppermost layer and the lowermost layer, signal wiring 15 and grounding pads 12 to 14 mounted on both sides of signal wiring 15 are provided. Then, FIG. 4 is a perspective view showing a specific configuration of intermediate layer 11. Signal wirings 15-1, 15-2 are conductors that can transmit signals of the circuit formed, for example, wiring about 100 μm wide formed with aluminum. A plurality of grounding pads 12 to 14 are terminals about 100 μm square formed by aluminum which are the same as signal wiring 15. Each grounding pad is connected to the grounding wiring (not illustrated) of still lower layer by via-holes (not illustrated) to maintain grounding potential. As clear from the figure, grounding pads 12 and 13 are mounted in the vicinity of wiring cut halfway of the central portion of intermediate layer 11. In addition, grounding pad 14 is mounted on the substrate edge of signal wiring 15. Signal wirings 15-1, 15-2 are not electrically connected as shown in region 21.

Figure 1:
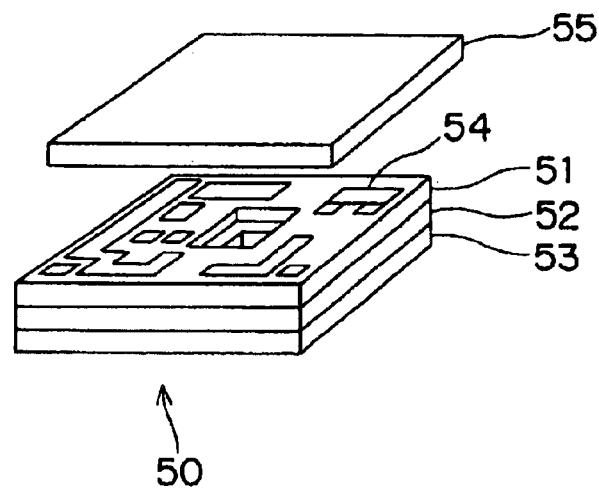
FIG. 1 is a perspective view of a conventional ceramic multilayer substrate.
Figure 2:
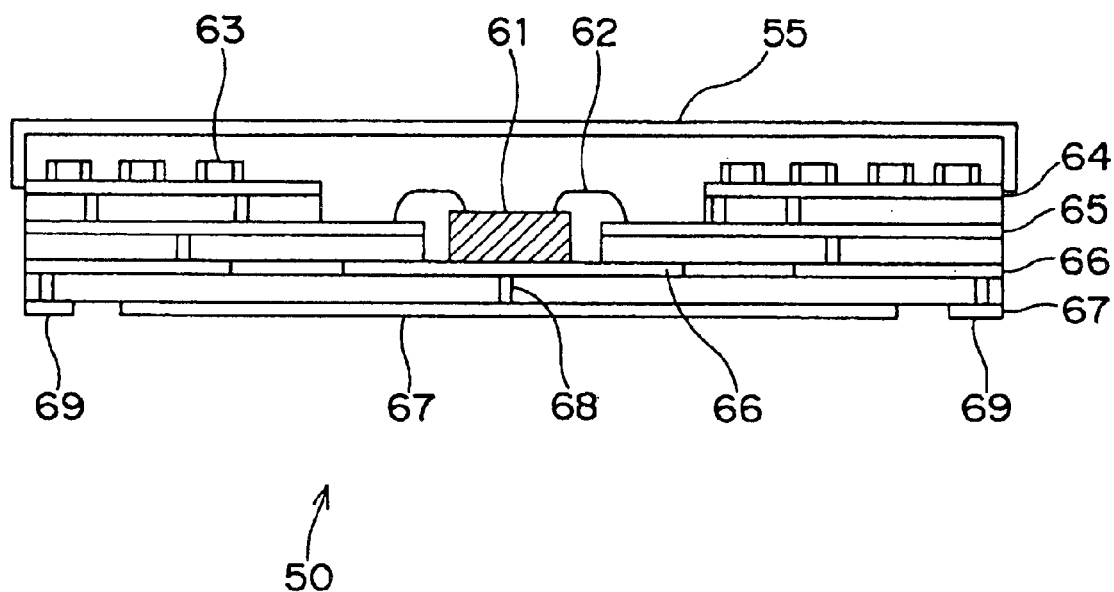
FIG. 2 is a cross-sectional view of a ceramic multilayer substrate cut in the direction perpendicular to each layer.

Now, principal features of the present invention will be described. The present invention relates to processing of inspecting the intermediate layer of a ceramic multilayer substrate with ceramic substrates laminated. In the present embodiment, a hole is bored in a substrate (hereinafter called the "upper layer substrate") located above intermediate layer 11 of the ceramic multilayer substrate, and from the hole, intermediate layer 11 is inspected. Consequently, in intermediate layer 11, grounding pads required for inspection are provided. In addition, because a hole is bored in the upper layer substrate of intermediate layer 11, signal wiring and chip parts, and other circuit elements are arranged with care to avoid the region where a hole is bored. Because in a conventional ceramic multilayer substrate 50 (FIGS. 1 and 2), the intermediate layer (intermediate layer 52 in FIG. 1) of the conventional ceramic multilayer substrate is unable to be directly inspected, needless to say, no grounding pad existed. In addition, since no hole is bored in the upper layer substrate of the intermediate layer, from the viewpoint of circuit element layout, the intermediate layer substrate and the upper layer substrate are designed independently.

The reasons for inspecting the intermediate layer are explained as follows. When the wiring is connected to the element that forms the circuit, it becomes a problem how much impedance is deviated. Depending on the impedance, there exists the oscillating frequency. The RF terminal of modules, etc. is designed to achieve, for example, about 50 ohm at the time of operation. This "50 ohm" means the center of the Smith chart that expresses impedance. However, even if wiring is designed to achieve 50 ohm impedance by connecting elements and wiring by simulation, when circuits are fabricated actually, impedance frequently deviates. This deviation increases particularly in the intermediate layer. Consequently, in the present invention, the intermediate layer is subject to the inspection.

Figure 5A:
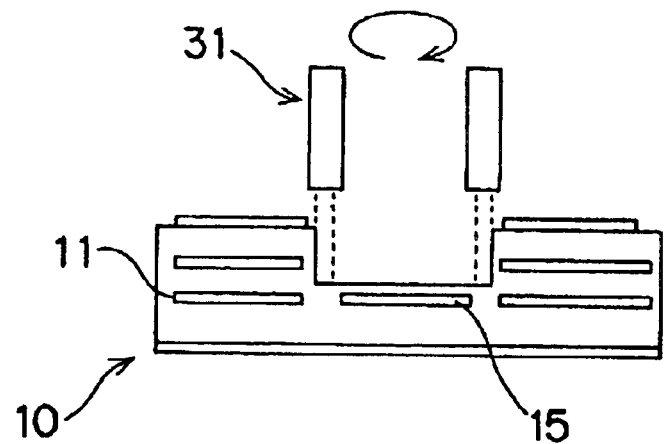
FIG. 5A is a diagram which shows a process for boring a hole using laser light.
Figure 5B:
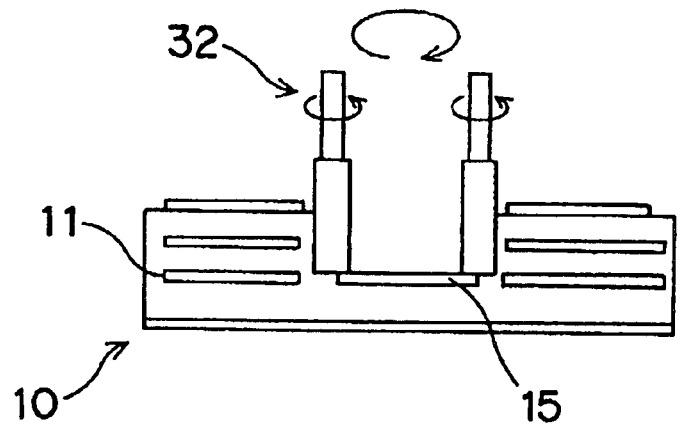
FIG. 5B is a diagram which shows a process for scraping wiring by diamond bar.
Figure 5C:
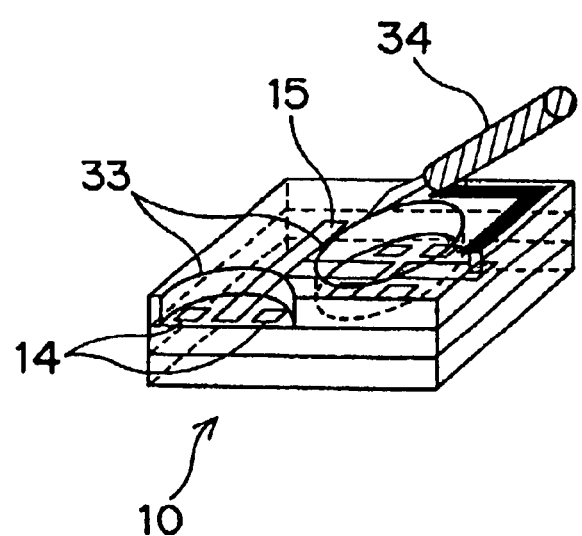
FIG. 5C is a diagram which shows an inspection process with a probe needle applied.

FIGS. 5A through 5C are diagrams showing the inspection technique of the intermediate layer by the present embodiment. To be more specific, FIG. 5A is a diagram showing a process for boring hole by laser 31. FIG. 5B is a diagram showing a process for scraping wiring 15 by diamond bar 32. FIG. 5C is a diagram showing a process of inspection with a probe needle applied. First of all, referring to FIG. 5A, excimer laser 31 is applied to the region of the upper layer substrate located above the grounding pad of intermediate layer 11, or region 21 (FIG. 4) and the upper layer substrate is scraped right before signal wiring 15 of intermediate layer 11. The term "right before" referred to herein means to the thickness that allows signal wiring 15 of intermediate layer 11 to be observed faintly, for example, 0.5 mm. As described above, to the relevant region to which laser is applied, it is designed not to allow circuit elements such as signal wirings and chip parts to exist. The reason why excimer laser 31 is used is because it can eliminate detrimental effects of heat on substrate and enables subtle processing. To be more specific, it is possible to process the substrate without damaging chip parts and other signal wiring on the upper layer substrate.

Referring now to FIG. 5B, for intermediate layer 11 scraped by excimer laser 31, using diamond bar 32 with a diamond mounted to the head end, which is a hard polishing tool, the upper layer substrate is polished until grounding pad 14 or signal wiring 15 of intermediate layer 11 appears, and a hole is bored. That is, the upper layer substrate is further scraped to bore a hole. For example, if the needle tip width of probe needle is 250 μm, a hole about 400 μm square or about 400 μm in diameter is bored. FIG. 5C shows hole 33 bored in this way. For example, it is understood that grounding pad 14 and signal wiring 15 existing between pads are exposed. As shown in the drawing, a plurality of holes may be bored simultaneously or successively. Because a hole is bored in the upper layer substrate using not only excimer laser 31 but also diamond bar 32, fine processing is definitely carried out and consequently, disconnection of signal wiring 15 of intermediate layer 11 would not result.

By bringing probe needle 34 in contact with grounding pads 12 through 14 and/or signal wiring 15 through the hole in the upper layer substrate bored as described above, characteristics, etc. of grounding pads 12 through 14 and signal wiring 15 and across circuits can be inspected by using microwave, for example. Note that, in the figure, probe needle 34 is drawn in a form of a bar tapered at the head end, but the known probe needle has three needles aligned in one row at specified intervals. Of these, needles on both ends are grounding needles and the needle at the center is the needle for wiring which is brought in contact with the wiring to be inspected. Since the known probe needle is configured in this way, grounding pads must be installed on both sides of signal wiring 15. As a result, characteristics of signal wiring 15 (for example, S parameter) and effects of wiring of semiconductor element can be evaluated.

To exemplify the evaluation procedure, first of all, prepare two probe needles and connect each probe needle to two RF connection terminals of the network analyzer, which is an S parameter measuring apparatus. Secondly, of the probe needles connected, bring the wiring needle at the center to wiring and grounding needles on both ends to grounding pads on both side of wiring. Thirdly, transmit wide-band frequency signals from the network analyzer and measure such as S parameter characteristics.

"S parameter" is used for evaluating circuit characteristics of high-frequency region. In general, in the high frequency, it is extremely difficult to measure voltage and current as in the case of low frequency. For example, bringing probes to wiring for voltage measurement causes the probe to function like a stab and changes the circuit configuration. Even if they are not brought in contact, bringing a substance which is located around the wiring pattern close to wiring and would disturb the electromagnetic field around the wiring pattern disturbs the characteristics of the circuit proper. Because even in the high-frequency region, the stably and accurately measurable amount is electric power, the circuit network can be treated as a black box even in the high frequency if the electric power entered in the circuit can be related to the electric power outputted. Therefore, it is useful to find the scattering matrix (S matrix) which specifies circuit characteristics in accord with the size and the phase of waves related to electric power inputted and outputted to and from each terminal pair (ports) of the circuit. And each element of S matrix is the S parameter referred to herein. Using the S parameter, it is possible to fabricate the specified circuit and adjust the S parameter to achieve the optimum characteristics of elements that compose the circuit.

Figure 6A:
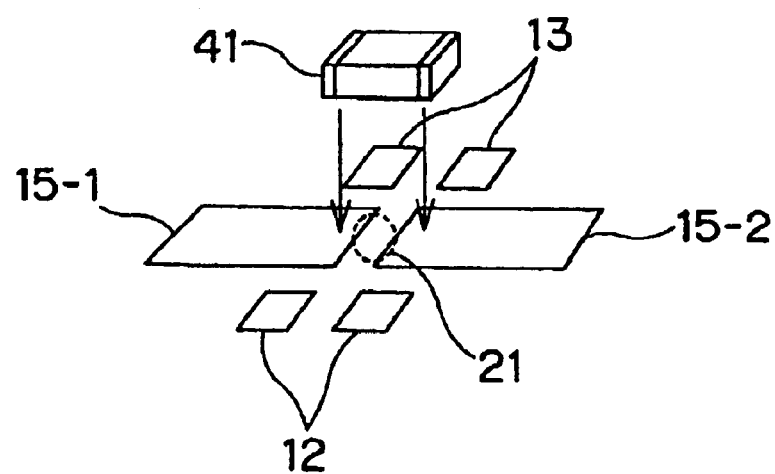
FIGS. 6A and 6B are schematic representations explaining a circuit that can be formed on the intermediate layer.
Figure 6B:
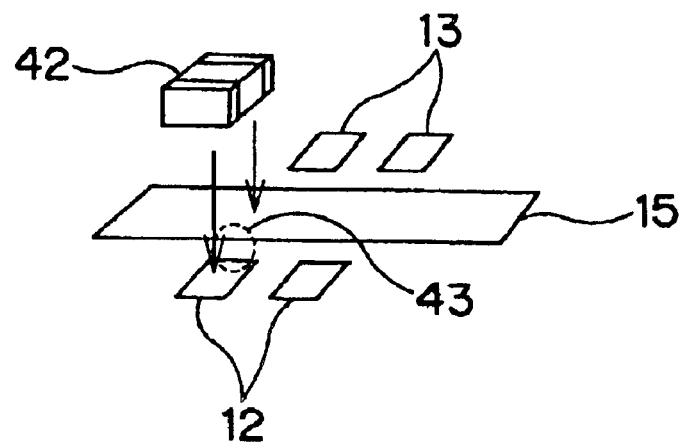

After evaluating the characteristics of signal wiring 15 of intermediate layer 11, a circuit can be newly formed on ceramic multilayer substrate 10 with a hole bored in the upper layer substrate. FIG. 6A and FIG. 6B are schematic representations explaining circuits that can be formed on intermediate layer 11. Referring to FIG. 6A, no electric continuity exists across signal wiring 15-1 and 15-2 because they are cut at region 21. That is, signal wiring 15-1 and 15-2 are isolated. However, no-resistant 0-ohm chip 41 or chip parts of resistance R, capacitance C, impedance L, etc. are mounted on region 21 so that they come in contact with both signal wiring 15-1 and 15-2. Therefore, signal wiring 15-1 and 15-2 may be able to function as one signal wiring. On the other hand, referring now to FIG. 6B, signal wiring 15 not cut may be connected to grounding pad 12. That is, non-resistance chip 42 or C.R.L chips may be provided on region 43 so that they connect to both of signal wiring 15 and grounding pad 12. Note that, in the example shown in FIG. 6A, grounding pad 12 and signal wiring 15-1 may be connected by chip 41. By mounting grounding pads in the vicinity of signal wiring of intermediate layer 11 in this way, new chips, etc. can be arranged and a circuit can be formed. For example, since parts with oscillation measures taken, parts for impedance adjustment, etc. can be added, the characteristics obtained by evaluation can be still more upgraded.

After completion of the evaluation of intermediate layer wiring as described above and forming a new circuit by the above-mentioned technique, if necessary, a cap is attached to the ceramic multilayer substrate to complete a semiconductor module. For the cap, cap 55 shown in FIGS. 1 and 2 can be used as in conventional cases.

The invention being thus described, it will be obvious that the same may be varied in many ways. Such variations are not to be regarded as a departure from the spirit and scope of the invention, and all such modifications as would be obvious to one skilled in the art are intended to be included within the cope of the following claims.

What is claimed is:

1. An evaluation method for evaluating characteristics of an intermediate layer circuit located between an uppermost layer and a lowermost layer of a multilayer substrate with multiple laminated substrates, wherein the intermediate layer circuit includes wiring and a grounding pad, at a grounding potential, located proximate the wiring, comprising:

irradiating a region of an upper layer substrate located opposite the grounding pad of the intermediate layer with a laser to ablate a thickness of material of the upper layer substrate;

polishing the upper layer substrate ablated with a polishing tool to expose at least one of the wiring and the grounding pad; and bringing a probe needle in contact with the at least one of the wiring exposed and the grounding pad exposed to evaluate characteristics of the intermediate layer circuit.

2. The evaluation method according to claim 1, wherein a circuit is located on the upper layer substrate, and the circuit is arranged to avoid the region of the upper layer substrate located opposite the grounding pad of the intermediate layer.

3. The evaluation method according to claim 2, including exposing both the wiring and the grounding pad, and electrically connecting the wiring exposed and the grounding pad exposed using a circuit element.

4. The evaluation method according to claim 2, wherein the wiring includes two wiring elements isolated from each other and exposed by ablation, and further comprising electrically connecting the exposed two wiring elements using a circuit element.

5. The evaluation method according to claim 2, including irradiating the region of the upper layer substrate with light from an excimer laser.

6. The evaluation method according to claim 2, including polishing with a diamond bar.

* * * * *